(12) United States Patent
Minagawa

(10) Patent No.: US 7,416,871 B2
(45) Date of Patent: Aug. 26, 2008

(54) THERMO-STABLE LACTATE OXIDASE

(75) Inventor: Hirotaka Minagawa, Tokyo (JP)

(73) Assignee: NEC Corporation, Tokyo (JP)

( * ) Notice: Subject to any disclaimer, the term of this patent is extended or adjusted under 35 U.S.C. 154(b) by 467 days.

(21) Appl. No.: 10/969,122

(22) Filed: Oct. 20, 2004

(65) Prior Publication Data

US 2005/0214917 A1 Sep. 29, 2005

(30) Foreign Application Priority Data

Oct. 21, 2003 (JP) .............................. 2003-360576

(51) Int. Cl.
- *C12N 9/02* (2006.01)
- *C12N 15/00* (2006.01)
- *C12N 1/20* (2006.01)
- *C07H 21/04* (2006.01)

(52) U.S. Cl. ............... 435/189; 435/320.1; 435/252.33; 536/23.2

(58) Field of Classification Search ................ 435/189, 435/320.1, 252.33; 536/23.2
See application file for complete search history.

(56) References Cited

FOREIGN PATENT DOCUMENTS

| JP | 4557/1983 | 1/1983 |
|---|---|---|
| JP | 10190/1984 | 3/1984 |
| JP | 177886/1990 | 7/1990 |
| JP | 8-511689 | 12/1996 |
| JP | 2624217 | 4/1997 |
| JP | 248574/1998 | 9/1998 |
| JP | 2001-086988 | 4/2001 |

OTHER PUBLICATIONS

Oikawa T. et al., "Chemo-Enzymatic D-Enantiomerization of DL-Lactate", *Biotechnology and Bioengineering*, 73(1):80-82 (2001).
Minagawa H. et al., "Development of Long Life Lactate Sensor Using Thermostable Mutant Lactate Oxidase", *Biosensors & Bioelectronics*, 13(3-4):313-318 (1998).
Zoller M.J. et al., "Oligonucleotide-Directed Mutagenesis Using M13-Derived Vectors: An Efficient and General Procedure for the Production of Point Mutations in any Fragment of DNA", *Nucleic Acids Research*, 10(20):6487-6500 (1982).
Dower W.J. et al., "High Efficiency Transformation of *E.coli* by High Voltage Electroporation", *Nucleic Acids Research*, 16(13):6127-6145 (1988).
Duncan J.D. et al., "Purification and Properties of *Aerococcus Viridans* Lactate Oxidase", *Biochemical and Biophysical Research Comunications*, 164(2):919-926 (1989).

*Primary Examiner*—Rebecca E. Prouty
*Assistant Examiner*—Malgorzata A. Walicka
(74) *Attorney, Agent, or Firm*—Scully, Scott, Murphy & Presser, P.C.

(57) ABSTRACT

A highly thermo-stable lactate oxidase has been provided by, in the lactate oxidase obtained from *Aerococcus viridans*, modifying the 6 amino acid residues.

3 Claims, 4 Drawing Sheets

Fig. 1 (a)

```
ATG AAT AAC AAT GAC ATT GAA TAT AAT GCA CCC AGT GAA ATC AAG TAC  48
MET Asn Asn Asn Asp Ile Glu Tyr Asn Ala Pro Ser Glu Ile Lys Tyr  16
ATT GAT GTT GTC AAT ACT TAT GAC TTA GAA GAA GAA GCA AGT AAA GTG  96
Ile Asp Val Val Asn Thr Tyr Asp Leu Glu Glu Glu Ala Ser Lys Val  32
GTA CCA CAT AGT GGT TTT AAC TAT ATT GCT GGT GCA TCT GGT GAT GAG 144
Val Pro His Ser Gly Phe Asn Tyr Ile Ala Gly Ala Ser Gly Asp Glu  48
TGG ACT AAA CGC GCT AAT GAC CGT GCA TGG AAA CAT AAA TTA CTG TAC 192
Trp Thr Lys Arg Ala Asn Asp Arg Ala Trp Lys His Lys Leu Leu Tyr  64
CCA CGT CTA GCG CAA GAT GTT GAA GCG CCC GAT ACA AGT ACT GAA ATT 240
Pro Arg Leu Ala Gln Asp Val Glu Ala Pro Asp Thr Ser Thr Glu Ile  80
TTA GGT CAT AAA ATT AAA GCC CCA TTC ATC ATG GCA CCA ATT GCT GCA 288
Leu Gly His Lys Ile Lys Ala Pro Phe Ile MET Ala Pro Ile Ala Ala  96
CAT GGT TTA GCC CAC ACT TCT AAA GAA GCT GGT ACT GCA CGT GCA GTT 336
His Gly Leu Ala His Thr Ser Lys Glu Ala Gly Thr Ala Arg Ala Val 112
TCA GAA TTT GGT ACA ATT ATG TCC ATC TCA GCT TAT TCT GGT GCA ACA 384
Ser Glu Phe Gly Thr Ile MET Ser Ile Ser Ala Tyr Ser Gly Ala Thr 128
TTT GAA GAA ATT TCT GAA GGC TTA AAT GGC GGA CCC CGT TGG TTC CAA 432
Phe Glu Glu Ile Ser Glu Gly Leu Asn Gly Gly Pro Arg Trp Phe Gln 144
ATC TAT ATG GCT AAA GAT GAC CAA CAA AAC CGT GAT ATC TTA GAC GGA 480
Ile Tyr MET Ala Lys Asp Asp Gln Gln Asn Arg Asp Ile Leu Asp Gly 160
GCT AAA TCT GAT GGT GCA ACT GCT ATC ATC CTT ACA GCT GAC TCA ACT 528
Ala Lys Ser Asp Gly Ala Thr Ala Ile Ile Leu Thr Ala Asp Ser Thr 176
GTT TCT GGA AAC CGT GAC CGT GAT GTG AAG AAT AAA TTC GTT TAC CCA 576
Val Ser Gly Asn Arg Asp Arg Asp Val Lys Asn Lys Phe Val Tyr Pro 192
TTT GGT ATG CCA ATT ATT CAA CGT TAC TTA CGC GGT ACA GCA GAG GGT 624
Phe Gly MET Pro Ile Ile Gln Arg Tyr Leu Arg Gly Thr Ala Glu Gly 208
```

Fig. 1 (b)

```
ATG TCA TTA AAC AAT ATC TAC GGA GCT TCA AAA CAA AAA ATC TCA CCA 672
MET Ser Leu Asn Asn Ile Tyr Gly Ala Ser Lys Gln Lys Ile Ser Pro 224
AGA GAT ATT GAG GAA ATC GCC TCT CAT TCT GGA TTA CCA GTA TTC GTT 720
Arg Asp Ile Glu Glu Ile Ala Ser His Ser Gly Leu Pro Val Phe Val 240
AAA GGT ATT CAA CAC CCA GAA GAT GCA GAT ATG GCA ATC AAA GCT GGT 768
Lys Gly Ile Gln His Pro Glu Asp Ala Asp MET Ala Ile Lys Ala Gly 256
GCA TCA GGT ATC TGG GTA TCT AAC CAC GGT GCT CGT CAA CTA TAT GAA 816
Ala Ser Gly Ile Trp Val Ser Asn His Gly Ala Arg Gln Leu Tyr Glu 272
GCT CCA GGT TCA TAT GAC ACC CTT CCA GCT ATT GCT GAA CGT GTA AAC 864
Ala Pro Gly Ser Tyr Asp Thr Leu Pro Ala Ile Ala Glu Arg Val Asn 288
AAA CGT GTA CCA ATC GTC TTT GAT TCA GGT GTA CGT CGT GGT GAA CAC 912
Lys Arg Val Pro Ile Val Phe Asp Ser Gly Val Arg Arg Gly Glu His 304
GTT GCC AAA GCG CTA GCT TCA GGG GCA GAC GTT GTT GCT TTA GGA CGC 960
Val Ala Lys Ala Leu Ala Ser Gly Ala Asp Val Val Ala Leu Gly Arg 320
CCA GTC TTA TTT GGT TTA GCT TTA GGT GGA TGG CAA GGT GCA TAC TCA 1008
Pro Val Leu Phe Gly Leu Ala Leu Gly Gly Trp Gln Gly Ala Tyr Ser 336
GTA CTT GAC TAC TTC CAA AAA GAC TTA ACA CGC GTA ATG CAA TTA ACA 1056
Val Leu Asp Tyr Phe Gln Lys Asp Leu Thr Arg Val MET Gln Leu Thr 352
GGT TCA CAA AAT GTG GAA GAC TTG AAG GGT CTA GAT TTA TTC GAT AAC 1104
Gly Ser Gln Asn Val Glu Asp Leu Lys Gly Leu Asp Leu Phe Asp Asn 368
CCA TAC GGT TAT GAA TAC 1122
Pro Tyr Gly Tyr Glu Tyr 374
```

Change of Residual Activity in Time Course under Heating at 70°C

1: Mutant LOD according to the present invention

2: Mutant LOD12

3: Wild-type LOD

SEQUENCE LISTING

<160> NUMBER OF SEQ ID NOS: 9

<210> SEQ ID NO 1

<211> LENGTH: 1122
<212> TYPE: DNA
<213> ORGANISM: Artificial Sequence
<220> FEATURE:
<223> OTHER INFORMATION: Artificial sequence derived from Aerococcus
      viridans

<400> SEQUENCE: 1

```
atg aat aac aat gac att gaa tat aat gca ccc agt gaa atc aag tac         48
MET Asn Asn Asn Asp Ile Glu Tyr Asn Ala Pro Ser Glu Ile Lys Tyr
 1               5                  10                  15 att gat gtt gtc aat act tat gac tta gaa gaa gaa gca agt aaa gtg         96
Ile Asp Val Val Asn Thr Tyr Asp Leu Glu Glu Glu Ala Ser Lys Val
             20                  25                  30 gta cca cat agt ggt ttt aac tat att gct ggt gca tct ggt gat gag        144
Val Pro His Ser Gly Phe Asn Tyr Ile Ala Gly Ala Ser Gly Asp Glu
         35                  40                  45 tgg act aaa cgc gct aat gac cgt gca tgg aaa cat aaa tta ctg tac        192
Trp Thr Lys Arg Ala Asn Asp Arg Ala Trp Lys His Lys Leu Leu Tyr
     50                  55                  60 cca cgt cta gcg caa gat gtt gaa gcg ccc gat aca agt act gaa att        240
Pro Arg Leu Ala Gln Asp Val Glu Ala Pro Asp Thr Ser Thr Glu Ile
 65                  70                  75                  80 tta ggt cat aaa att aaa gcc cca ttc atc atg gca cca att gct gca        288
Leu Gly His Lys Ile Lys Ala Pro Phe Ile MET Ala Pro Ile Ala Ala
                 85                  90                  95 cat ggt tta gcc cac act tct aaa gaa gct ggt act gca cgt gca gtt        336
His Gly Leu Ala His Thr Ser Lys Glu Ala Gly Thr Ala Arg Ala Val
            100                 105                 110 tca gaa ttt ggt aca att atg tcc atc tca gct tat tct ggt gca aca        384
Ser Glu Phe Gly Thr Ile MET Ser Ile Ser Ala Tyr Ser Gly Ala Thr
        115                 120                 125 ttt gaa gaa att tct gaa ggc tta aat ggc gga ccc cgt tgg ttc caa        432
Phe Glu Glu Ile Ser Glu Gly Leu Asn Gly Gly Pro Arg Trp Phe Gln
    130                 135                 140 atc tat atg gct aaa gat gac caa caa aac cgt gat atc tta gac gga        480
Ile Tyr MET Ala Lys Asp Asp Gln Gln Asn Arg Asp Ile Leu Asp Gly
145                 150                 155                 160 gct aaa tct gat ggt gca act gct atc atc ctt aca gct gac tca act        528
Ala Lys Ser Asp Gly Ala Thr Ala Ile Ile Leu Thr Ala Asp Ser Thr
                165                 170                 175 gtt tct gga aac cgt gac cgt gat gtg aag aat aaa ttc gtt tac cca        576
Val Ser Gly Asn Arg Asp Arg Asp Val Lys Asn Lys Phe Val Tyr Pro
            180                 185                 190 ttt ggt atg cca att att caa cgt tac tta cgc ggt aca gca gag ggt        624
Phe Gly MET Pro Ile Ile Gln Arg Tyr Leu Arg Gly Thr Ala Glu Gly
        195                 200                 205 atg tca tta aac aat atc tac gga gct tca aaa caa aaa atc tca cca        672
MET Ser Leu Asn Asn Ile Tyr Gly Ala Ser Lys Gln Lys Ile Ser Pro
    210                 215                 220 aga gat att gag gaa atc gcc tct cat tct gga tta cca gta ttc gtt        720
Arg Asp Ile Glu Glu Ile Ala Ser His Ser Gly Leu Pro Val Phe Val
225                 230                 235                 240 aaa ggt att caa cac cca gaa gat gca gat atg gca atc aaa gct ggt        768
Lys Gly Ile Gln His Pro Glu Asp Ala Asp MET Ala Ile Lys Ala Gly
                245                 250                 255 gca tca ggt atc tgg gta tct aac cac ggt gct cgt caa cta tat gaa        816
Ala Ser Gly Ile Trp Val Ser Asn His Gly Ala Arg Gln Leu Tyr Glu
            260                 265                 270 gct cca ggt tca tat gac acc ctt cca gct att gct gaa cgt gta aac        864
Ala Pro Gly Ser Tyr Asp Thr Leu Pro Ala Ile Ala Glu Arg Val Asn
        275                 280                 285
```

```
aaa cgt gta cca atc gtc ttt gat tca ggt gta cgt cgt ggt gaa cac      912
Lys Arg Val Pro Ile Val Phe Asp Ser Gly Val Arg Arg Gly Glu His
    290                 295                 300 gtt gcc aaa gcg cta gct tca ggg gca gac gtt gtt gct tta gga cgc      960
Val Ala Lys Ala Leu Ala Ser Gly Ala Asp Val Val Ala Leu Gly Arg
305                 310                 315                 320 cca gtc tta ttt ggt tta gct tta gga tgg caa ggt gca tac tca         1008
Pro Val Leu Phe Gly Leu Ala Leu Gly Gly Trp Gln Gly Ala Tyr Ser
                325                 330                 335 gta ctt gac tac ttc caa aaa gac tta aca cgc gta atg caa tta aca     1056
Val Leu Asp Tyr Phe Gln Lys Asp Leu Thr Arg Val MET Gln Leu Thr
                340                 345                 350 ggt tca caa aat gtg gaa gac ttg aag ggt cta gat tta ttc gat aac     1104
Gly Ser Gln Asn Val Glu Asp Leu Lys Gly Leu Asp Leu Phe Asp Asn
            355                 360                 365 cca tac ggt tat gaa tac                                             1122
Pro Tyr Gly Tyr Glu Tyr
    370

<210> SEQ ID NO 2
<211> LENGTH: 32
<212> TYPE: DNA
<213> ORGANISM: Artificial Sequence
<220> FEATURE:
<223> OTHER INFORMATION: Description of Artificial sequence:sense primer

<400> SEQUENCE: 2
gtggtaccac atagtggttt aactatatt gc                                   32

<210> SEQ ID NO 3
<211> LENGTH: 31
<212> TYPE: DNA
<213> ORGANISM: Artificial Sequence
<220> FEATURE:
<223> OTHER INFORMATION: Description of Artificial sequence:sense primer

<400> SEQUENCE: 3
gtttagccca cacttctaaa gaagctggta c                                   31

<210> SEQ ID NO 4
<211> LENGTH: 37
<212> TYPE: DNA
<213> ORGANISM: Artificial Sequence
<220> FEATURE:
<223> OTHER INFORMATION: Description of Artificial sequence:sense primer

<400> SEQUENCE: 4
gatattgagg aaatcgcctc tcattctgga ttaccag                             37

<210> SEQ ID NO 5
<211> LENGTH: 37
<212> TYPE: DNA
<213> ORGANISM: Artificial Sequence
<220> FEATURE:
<223> OTHER INFORMATION: Description of Artificial sequence:sense primer

<400> SEQUENCE: 5
gaagctccag gttcatatga caccttcca gctattg                              37

<210> SEQ ID NO 6
<211> LENGTH: 32
<212> TYPE: DNA
<213> ORGANISM: Artificial Sequence
<220> FEATURE:
<223> OTHER INFORMATION: Description of Artificial sequence:anti-sense
```

```
                                 -continued
         primer

<400> SEQUENCE: 6
gcaatatagt taaaaccact atgtggtacc ac                                    32

<210> SEQ ID NO 7
<211> LENGTH: 31
<212> TYPE: DNA
<213> ORGANISM: Artificial Sequence
<220> FEATURE:
<223> OTHER INFORMATION: Description of Artificial sequence:anti-sense
      primer

<400> SEQUENCE: 7
gtaccagctt ctttagaagt gtgggctaaa c                                     31

<210> SEQ ID NO 8
<211> LENGTH: 37
<212> TYPE: DNA
<213> ORGANISM: Artificial Sequence
<220> FEATURE:
<223> OTHER INFORMATION: Description of Artificial sequence:anti-sense
      primer

<400> SEQUENCE: 8
ctggtaatcc agaatgagag gcgatttcct caatatc                               37

<210> SEQ ID NO 9
<211> LENGTH: 37
<212> TYPE: DNA
<213> ORGANISM: Artificial Sequence
<220> FEATURE:
<223> OTHER INFORMATION: Description of Artificial sequence:anti-sense
      primer

<400> SEQUENCE: 9
caatagctgg aagggtgtca tatgaacctg gagcttc                               37
```

THERMO-STABLE LACTATE OXIDASE

FIELD OF THE INVENTION

The present invention relates to a lactate oxidase, which catalyzes a reaction represented by the following reaction formula:

L-lactate+oxygen→pyruvic acid+hydrogen peroxide

More particularly, the present invention relates to a highly thermo-stable lactate oxidase.

DESCRIPTION OF THE RELATED ART

Lactate oxidase is an enzyme which catalyzes the formation of pyruvic acid and hydrogen peroxide from L-lactic acid and oxygen, and is very useful in the measurement of lactic acid concentration in body fluid (e.g. blood) or in fermented food production process and also useful in the selective synthesis of D-lactic acid (which is useful as a starting substance of chiral compound) from DL-lactic acid (which is a racemic modification) (Tadao Oikawa; Shuji Mukoyama; Kenji Soda; Biotechnology and Bioengineering, 2001, Vol. 73, Issue 1, pp. 80-82).

The enzyme has been known to be present in, for example, bacteria belonging to *Pediococcus* genus, *Streptococcus* genus, *Aerococcus* genus and *Lactococcus* genus (Japanese Patent Publication No. 4557/1983 (JP-B-1983-4557); Japanese Patent Publication No. 10190/1984 (JP-B-1984-10190); Japanese Patent Laid-Open No. 177886/1990 (JP-A-1990-177886); and Japanese Patent Laid-Open No. 248574/1998 (JP-A-1998-248574)).

The present inventors previously disclosed a plurality of thermo-stable mutant as the lactate oxidase (Japanese Patent No. 2624217 and Japanese Patent Laid-Open No. 2001-086988 (JP-A-2001-096988).

The enzymes according to these conventional arts, however, have insufficient thermo-stability in some cases. That is, the lactate oxidase obtained from *Streptococcus* is low in thermo-stability and is quickly deactivated at temperatures higher than 34° C., according to the description of JP-B-1983-4557; the thermo stability of the lactate oxidase obtained from *Lactococcus* is 50° C. or lower, according to the description of JP-A-1998-248574; and even the lactate oxidase of highest thermo stability obtained from *Aerococcus* has a low residual activity of 5% or less when subjected to a thermo treatment of 65° C.×10 minutes, according to the description of JP-B-1984-10190. The present inventors improved conventional enzymes and disclosed the results in Japanese Patent No. 2624217 and JP-A-2001-096988. However, for application to, for example, a lactate sensor, more higher thermo stability is believed to be necessary (Minagawa H, Nakayama N, Matsmoto T, Ito N, Biosensors & Bioelectronics, 1998, Vol. 13, pp. 313-318).

SUMMARY OF THE INVENTION

A main object of the present invention is to develop a lactate oxidase having strikingly high thermo-stability as a result of addition of one or more mutation to the lactate oxidase (LOD12) enzyme described in Japanese Patent Laid-Open No. 2001-086988.

The present invention provides techniques relating to the following matters:

1. A lactate oxidase having an amino acid sequence shown below in SEQ ID NO: 1 (encoded by SEQ ID NO: 10).
2. A lactate oxidase according to the above section 1, which is capable of catalysis in a reaction represented by the following reaction formula;

L-lactic acid+oxygen→pyruvic acid+hydrogen peroxide

3. A lactate oxidase having an mutant amino acid, which is obtainable by subjecting deletion, substitution or addition of one or more amino acids to SEQ ID NO: 1 so as to maintain or improve the thermo-stability and the enzyme activity of the lactate oxidase having the amino acid sequence of SEQ ID NO: 1.
4. A vector comprising a gene, such as a DNA molecule, encoding the lactate oxidase of the above section 1 or the mutant lactate oxidase of the above section 3.

```
SEQ ID NO: 1
Met Asn Asn Asn Asp Ile Glu Tyr Asn Ala Pro Ser Glu Ile Lys Tyr Ile Asp Val Val   20

Asn Thr Tyr Asp Leu Glu Glu Glu Ala Ser Lys Val Val Pro His Ser Gly Phe Asn Tyr   40

Ile Ala Gly Ala Ser Gly Asp Glu Trp Thr Lys Arg Ala Asn Asp Arg Ala Trp Lys His   60

Lys Leu Leu Tyr Pro Arg Leu Ala Gln Asp Val Glu Ala Pro Asp Thr Ser Thr Glu Ile   80

Leu Gly His Lys Ile Lys Ala Pro Phe Ile Met Ala Pro Ile Ala Ala His Gly Leu Ala  100

His Thr Ser Lys Glu Ala Gly Thr Ala Arg Ala Val Ser Glu Phe Gly Thr Ile Met Ser  120

Ile Ser Ala Tyr Ser Gly Ata Thr Phe Glu Glu Ile Ser Glu Gly Leu Asn Gly Gly Pro  140

Arg Trp Phe Gln Ile Tyr MET Ala Lys Asp Asp Gln Gln Asn Arg Asp Ile Leu Asp Gly  160

Ala Lys Ser Asp Gly Ala Thr Ala Ile Ile Leu Thr Ala Asp Ser Thr Val Ser Gly Asn  180

Arg Asp Arg Asp Val Lys Asn Lys Phe Val Tyr Pro Phe Gly Met Pro Ile Ile Gln Arg  200

Tyr Leu Arg Gly Thr Ala Glu Gly Met Ser Leu Asn Asn Ile Tyr Gly Ala Ser Lys Gln  220

Lys Ile Ser Pro Arg Asp Ile Glu Glu Ile Ala Ser His Ser Gly Leu Pro Val Phe Val  240

Lys Gly Ile Gln His Pro Glu Asp Ala Asp MET Ala Ile Lys Ala Gly Ala Ser Gly Ile  260
```

```
                              -continued
Trp Val Ser Asn His Gly Ala Arg Gln Leu Tyr Glu Ala Pro Gly Ser Tyr Asp Thr Leu  280

Pro Ala Ile Ala Glu Arg Val Asn Lys Arg Val Pro Ile Val Phe Asp Ser Gly Val Arg  300

Arg Gly Glu His Val Ala Lys Ala Leu Ala Ser Gly Ala Asp Val Val Ala Leu Gly Arg  320

Pro Val Leu Phe Gly Leu Ala Leu Gly Gly Trp Gln Gly Ala Tyr Ser Val Leu Asp Tyr  340

Phe Gln Lys Asp Leu Thr Arg Val Met Gln Leu Thr Gly Ser Gln Asn Val Glu Asp Leu  360

Lys Gly Leu Asp Leu Phe Asp Asn Pro Tyr Gly Tyr Glu Tyr  374
```

The present inventors made a study on the above-mentioned tasks in order to enhance the thermo-stability of the lactate oxidases. As a result, the present inventors have found that the lactate oxidase having the above-mentioned amino acid sequence has strikingly high thermo-stability as compared with conventional lactate oxidases, and actually produced a lactate oxidase having an amino acid sequence of SEQ ID NO: 1.

FIG. 1 shows the gene sequence and the amino acid sequence of the lactate oxidase according to the present invention, wherein the underlined parts of the amino acid sequence portion are different from the wild-type lactate oxidase obtained from *Aerococcus*.

FIG. 2 shows the changes of the residual activities of a wild-type lactate oxidase, the thermo-stable described in JP-A-2001-096988 and the lactate oxidase of the present invention, according to a time course, when they were held at 70° C. It has been revealed that the lactate oxidase of the present invention, as compared with the wild-type lactate oxidase and the thermo-stable mutant lactate oxidase described in JP-A-2001-096988, has strikingly high thermo stability.

BRIEF DESCRIPTION OF THE DRAWINGS

FIG. 1(*a*) shows the gene sequence and the amino acid sequence of the lactate oxidase of the present invention, which continue FIG. 1(*b*).

FIG. 1(*b*) shows the gene sequence and the amino acid sequence of the lactate oxidase of the present invention.

DETAILED DESCRIPTION OF THE INVENTION AND PREFERRED EMBODIMENTS

The gene of the thermo-stable lactate oxidase of the present invention can be produced by using, as a template, the gene of the lactate oxidase derived from *Aerococcus viridans* or the pLOD 12 described in JP-A-2001-096988 and employing the site-directed mutagenesis as a publicly-known technique. The site-directed mutagenesis is a well-known technique in the related field, for which reference is made to, for example, Nucl. Acid Research, 1982, Vol. 10, pp. 6487-6500. The produced gene of the thermo-stable lactate oxidase of the present invention is inserted into a vector having an appropriate promoter (e.g. tac promoter or lac promoter) and an antibiotic-resistant marker (e.g. Ampicillin, Kanamycin or Tetracycline); an appropriate host (e.g. *Escherichia coli*) is transformed; then, a protein is expressed and purified by, for example, a method described in Japanese Patent No. 2624217; thereby, the thermo-stable lactate oxidase of the present invention can be obtained.

The mode for carrying out the invention is described in the following Example.

EXAMPLE

[Production of Gene of Thermo-stable Lactate Oxidase]

The gene of the thermo-stable lactate oxidase of the present invention was produced from the gene of the thermo-stable mutant lactate oxidase described in JP-A-2001-096988 by employing the site-directed mutagenesis, which is a known technique. Specifically explaining, the site-directed mutagenesis was repeated using a vector pLOD 12 containing a LOD 12 gene, as a template, and each of the pairs of primers (FWG36S and REG36S; FWT103S and RET103S; FWA232S and REA232S; and FWF277Y and REF277Y), independently. The primers have been selected from the four sense primers [FWG36S (SEQ ID NO: 2), FWT103S (SEQ ID NO: 3), FWA232S (SEQ ID NO: 4) and FWF277Y (SEQ ID NO: 5)] and 4 kinds of antisense primers [REG36S (SEQ ID NO: 6), RET103S (SEQ ID NO: 7), REA232S (SEQ ID NO: 8) and REF277Y (SEQ ID NO: 9)], which have been designed so as to give rise to intended mutation, whereby an intended mutant gene can be obtained.

```
Sequences of the primers
SEQ ID NO: 2
5'-GTGGTACCACATAGTGGTTTTAACTATATTGC-3'

SEQ ID NO: 3
5'-GTTTAGCCCACACTTCTAAAGAAGCTGGTAC-3'

SEQ ID NO: 4
5'-GATATTGAGGAAATCGCCTCTCATTCTGGATTACCAG-3'

SEQ ID NO: 5
5'-GAAGCTCCAGGTTCATATGACACCCTTCCAGCTATTG-3'

SEQ ID NO: 6
5'-GCAATATAGTTAAAACCACTATGTGGTACCAC-3'

SEQ ID NO: 7
5'-GTACCAGCTTCTTTAGAAGTGTGGGCTAAAC-3'

SEQ ID NO: 8
5'-CTGGTAATCCAGAATGAGAGGCGATTTCCTCAATATC-3'

SEQ ID NO: 9
5'-CAATAGCTGGAAGGGTGTCATATGAACCTGGAGCTTC-3'
```

Figure 3:
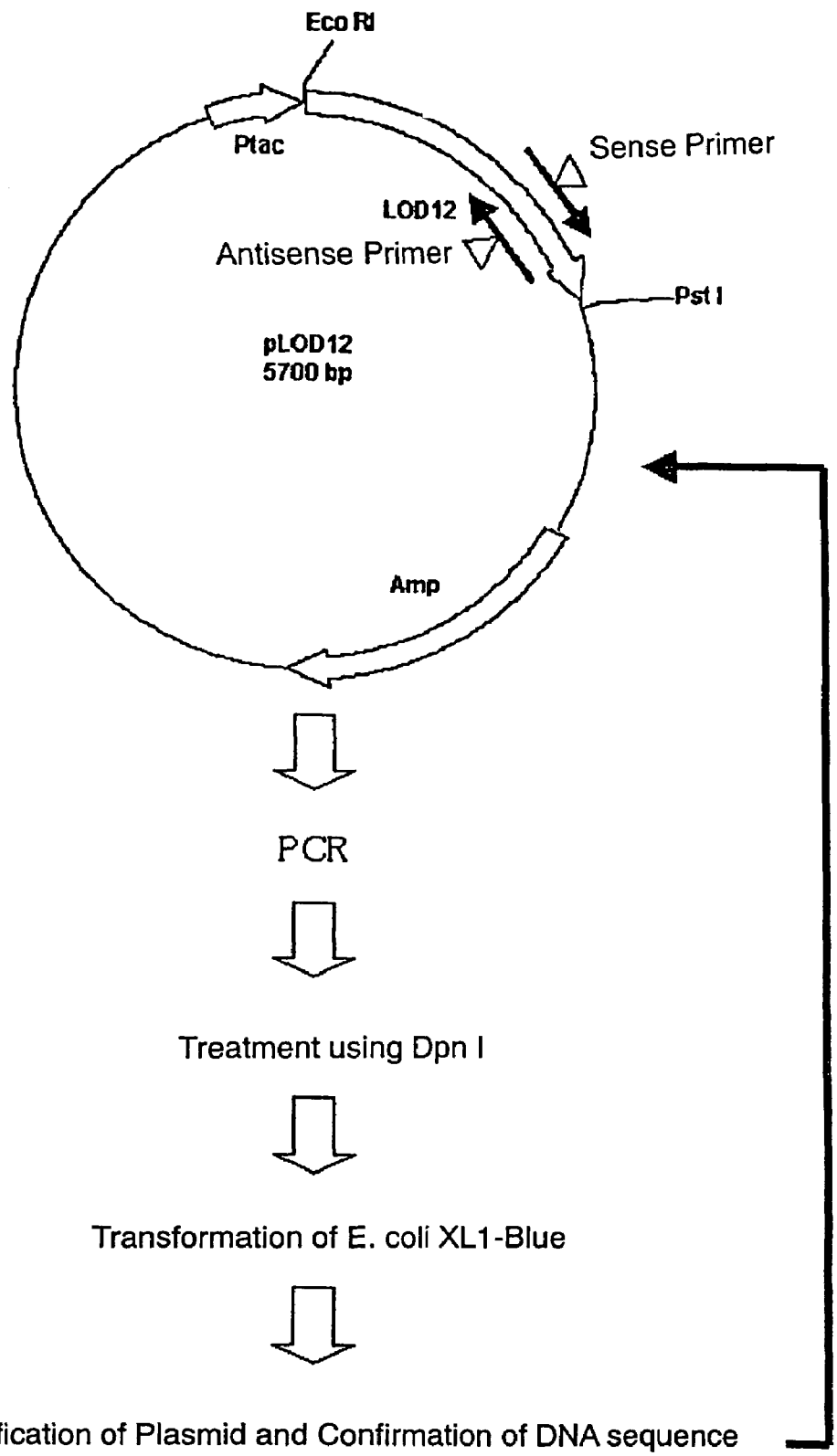
FIG. 3 shows a process for production of the gene of the lactate oxidase of the present invention.

Using 0.1 μg of one of the above primer pairs and 0.1 μg of the pLOD 12, PCR by Pfu polymerase was conducted using Quick Change Mutagenesis Kit (a product of STRATGENE, Funakoshi), after which the PCR product was treated at 37° C. for 1 hour using Dpn I. Using this Dpn I-treated PCR product, *E. coli* XL1-Blue was transformed, and the transformant was cultured at 37° C. overnight in an Ampicillin-containing LB agar medium (1% tryptone, 0.5% yeast extract, 0.5% NaCl, 1.5% agar, 0.01% ampicillin sodium). The resulting colonies were cultured at 37° C. overnight in an Ampicillin-containing LB liquid medium ((1% tryptone, 0.5% yeast extract, 0.5% NaCl, 0.01% Ampicillin). A plasmid was extracted and purified using a QIAGENE plasmid purification kit (a product of QIAGENE). The nucleotide sequence of the related enzyme portion of the plasmid obtained was confirmed using a DNA sequencer (ABI 373, a product of Applied Biosystems). The above site-directed mutagenesis was repeated using this plasmid as a template and also other primer pair described above, to obtain an intended mutant plasmid. For detail, reference is made to FIG. 3. The thus-obtained plasmid containing a mutant lactate oxidase gene was named pLOD 17.

[Expression of Thermo-stable Lactate Oxidase and Production of Enzyme Solution]

Using each 10 ng of pLOD 17, pLOD 12 and pLODwt (pLODwt is a plasmid which contains the wild-type lactate oxidase gene obtained from *Aerococcus* and whose other portions are the same as in pLOD 17 and pLOD 12), *E. coli* JM 109 was transformed by electroporation according to the method by Dower et al. (Dower et al., Nucleic Acids Research, 1988, Vol. 16, No. 13, pp. 6123-6145). Specifically explaining, the plasmid and *E. coli* JM 109 were mixed and the mixture was allowed to stand in ice for 1 minute. Then, introduction of gene was conducted by electroporation using Gene Pulser™ (a product of Bio Rad) under the conditions of 200 Ω, 25 µF and 18 kV/cm. Thereafter, the cells were cultured at 37° C. for 1 hour in a SOC medium (2% tryptone, 0.5% yeast extract, 10 mM NaCl, 2.5 mM KCl, 10 mM $MgCl_2$, 10 mM $MgSO_4$, 20 mM glucose). After the culture, the cells were sowed into a LAH medium (1% tryptone, 0.5% yeast extract, 0.5% NaCl, 1.5% agar, 0.01% Ampicillin sodium, 0.01% ABTS, 50 mM lithium L-lactate, 1 U/ml horse radish peroxidase), followed by culturing at 37° C. overnight. The resulting colonies were picked up with a sterilized toothpick and inoculated into 4 ml of a LA medium (1% tryptone, 0.5% yeast extract, 0.5% NaCl, 0.01% Ampicillin sodium), followed by culturing at 37° C. for 8 hours. Then, 1 ml of the resulting culture solution was added to 100 ml of a LA medium, followed by culturing at 37° C. overnight. Thereto was added 100 µl of 100 mM IPTG (isopropyl thiogalactopyranoside), followed by culturing at 37° C. for 3 hours. The cells were collected by centrifugation (12,000 rpm and 5 minutes), then washed with 10 ml of a potassium phosphate buffer solution (50 mM $KH_2PO_4/K_2HPO_4$, pH 7.1), and suspended in 10 ml of a buffer solution having the same composition. To the cell suspension were added PMSF (phenylmethylsulfonyl fluoride) and ethylenediaminetetraacetic acid (EDTA) so as to obtain a final concentration of 1 mM. The resulting mixture was subjected to a ultrasonic treatment (VP-60, a product of TAITEC) in ice. The cell debris generated was removed by centrifugation of 10 minutes. While the supernatant liquid after centrifugation were slowly stirred in ice, ammonium sulfate $[(NH_4)_2SO_4]$ was added thereto until it reached 50% saturation, followed by stirring for 30 minutes. Centrifugation was made at 12,000 rpm for 10 minutes to collect a precipitate. The precipitate was dissolved in a potassium buffer solution A (50 mM $KH_2PO_4/K_2HPO_4$, 100 mM KCl, pH 7.1). The resulting solution was passed through Sephadex G 25 (Amacham Pharmacia) equilibrated with the potassium buffer solution A for desalting. The desalted sample was passed through an anion exchange column, Q-Sepharorse FF (Amacham Pharmacia) equilibrated with the potassium buffer solution A, and elution was conducted using a potassium buffer solution B (50 mM $KH_2PO_4/K_2HPO_4$, 500 mM KCl, pH 7.1) by continuous gradation of salt concentration, to collect a fraction exhibiting an activity of lactate oxidase. The fraction was passed through a hydrophobic column, Phenylsepharose (Amacham Pharmacia) equilibrated with the potassium buffer solution B, and elution was conducted using the potassium buffer solution A, to collect a fraction exhibiting an activity of lactate oxidase. The thus-purified lactate oxidase showed a single band in electrophoresis of SDS polyacrylamide gel. The concentration of lactate oxidase was measured using BCA Protein Assay Kit (a product of Pierce and Takara Shuzo Co., Ltd.) and, as a standard, bovine serum albumin (BSA). The protein concentrations of LOD 17 (the lactate oxidase according to the present invention), LOD 12 (the thermo-stable lactate oxidase described in JP-A-2001-096988) and LODwt (the wild-type lactate oxidase obtained from *Aerococcus*) were adjusted each to 50 µg/ml, after which the activity of each lactate oxidase was measured.

[Measurement of Lactate Oxidase Activities]

Using the LOD 17 as the lactate oxidase according to the present invention; the LOD 12; and the LODwt as the comparative lactate oxidase samples to that according to the present invention, measurement of each activity was made according to the method by Duncan et al. (Duncan et al., B.B.R.C., 1989, Vol. 164, No. 2, pp. 919-926).

Figure 2:
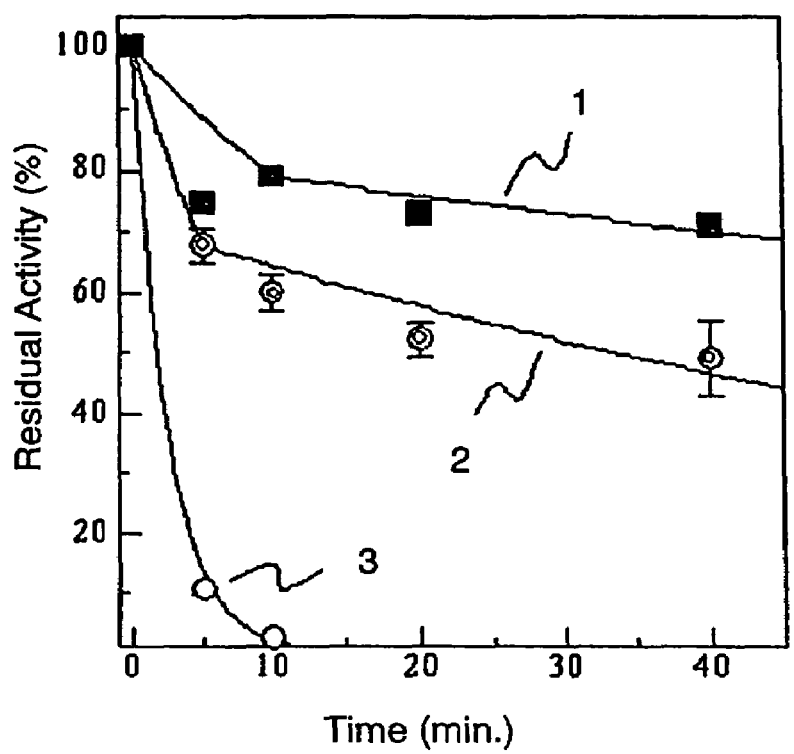
FIG. 2 shows the thermo-stability of the lactate oxidase of the present invention.

To 2.7 ml of pure water were added 120 µl of a HEPES buffer solution (1 M, pH 7.3), 30 µl of lithium L-lactate (96 mg/ml), 30 µl of 4-aminoantipyrine (30 mg/ml), 30 µl of phenol (31 mg/ml) and 60 µl of HRP (horseradish peroxide) (100 U/ml), followed by mixing. The mixture was placed in a cuvet having an optical path of 1 cm. Thereto was added 60 µl of a lactate oxidase solution, followed by stirring. Immediately, the mixture was measured in a time course for the change of 500 nm absorbance, using an absorptiometer (UV-365, a product of Shimadzu Corporation). The enzyme solution was allowed to stand in a thermostat of 70° C. for a given length of time (5, 10, 20 and 40 minutes) and then stand in ice to measure the enzymatic activity (residual activity). In FIG. 2 are shown the changes with time of the 70° C. residual activities of LODwt (the wild-type lactate oxidase obtained from *Aerococcus*), LOD 12 (the thermo-stable lactate oxidase described in JP-A-2001-096988) and the lactate oxidase of the present invention.

According to FIG. 2, the 70° C. residual activity of the wild-type LOD decreases to 0% after 10 minutes. Meanwhile, when the residual activities of the LOD 12 (the lactate oxidase of highest thermo stability obtained from *Aerococcus*) and the lactate oxidase of the present invention was compared with each other, the residual activity of the lactate oxidase of the present invention was higher than that of the LOD 12 after all holding times. Thus, a highly thermo-stable lactate oxidase can be obtained by the present invention.

What is claimed is:

1. An isolated lactate oxidase comprising the amino acid sequence set forth in SEQ ID NO: 1.

2. An isolated DNA molecule encoding a lactate oxidase according to claim 1 [or 2].

3. A vector comprising the DNA set forth in claim 2.

* * * * *